(12) United States Patent
Deal

(10) Patent No.: US 8,067,750 B2
(45) Date of Patent: Nov. 29, 2011

(54) AREA STERILIZER AND METHOD OF DISINFECTION

(76) Inventor: Jeffery L. Deal, Charleston, SC (US)

( * ) Notice: Subject to any disclaimer, the term of this patent is extended or adjusted under 35 U.S.C. 154(b) by 359 days.

(21) Appl. No.: 12/361,810

(22) Filed: Jan. 29, 2009

(65) Prior Publication Data

US 2009/0191100 A1 Jul. 30, 2009

Related U.S. Application Data

(60) Provisional application No. 61/024,373, filed on Jan. 29, 2008, provisional application No. 61/083,590, filed on Jul. 25, 2008.

(51) Int. Cl.
A61L 2/10 (2006.01)
A61L 9/20 (2006.01)
G21K 5/02 (2006.01)

(52) U.S. Cl. ......... 250/455.11; 250/453.11; 250/454.11; 250/504 R; 422/1; 422/3; 422/22; 422/24

(58) Field of Classification Search .............. 422/1, 3, 422/22, 24; 250/453.11, 454.11, 455.11, 250/493.1, 504 R
See application file for complete search history.

(56) References Cited

U.S. PATENT DOCUMENTS

| 3,418,069 | A | 12/1968 | Decupper |
| 3,576,593 | A | 4/1971 | Cicirello |
| 3,674,421 | A | 7/1972 | Decupper |
| 5,434,419 | A | 7/1995 | Decupper |
| 5,891,399 | A * | 4/1999 | Owesen ................. 422/121 |
| 6,139,803 | A * | 10/2000 | Watanabe et al. ......... 422/121 |
| 6,315,955 | B1 * | 11/2001 | Klein ...................... 422/73 |
| 6,433,343 | B1 | 8/2002 | Cimino et al. |
| 6,656,424 | B1 * | 12/2003 | Deal ......................... 422/3 |
| 2004/0009091 | A1 * | 1/2004 | Deal et al. ................. 422/3 |
| 2009/0004046 | A1 * | 1/2009 | McEllen .................... 422/2 |

* cited by examiner

Primary Examiner — Robert Kim
Assistant Examiner — Nicole Ippolito Rausch
(74) Attorney, Agent, or Firm — B. Craig Killough

(57) ABSTRACT

An ultraviolet area sterilizer or disinfector is incorporated into a building structure where concern exists regarding the presence of pathogenic bacteria on environmental surfaces. Ultraviolet C (UV-C) generators generate UV-C that is directed to architectural partitions of an enclosed area. The architectural partitions reflect UV-C to kill pathogens in the enclosed area. The device transmits a calculated dose of UV-C from a fixture mounted to an architectural partition in the enclosed area. Once an effective cumulative dose of UV-C has been reflected to radiation sensors, as measured by the sensors, the device shuts down.

18 Claims, 5 Drawing Sheets

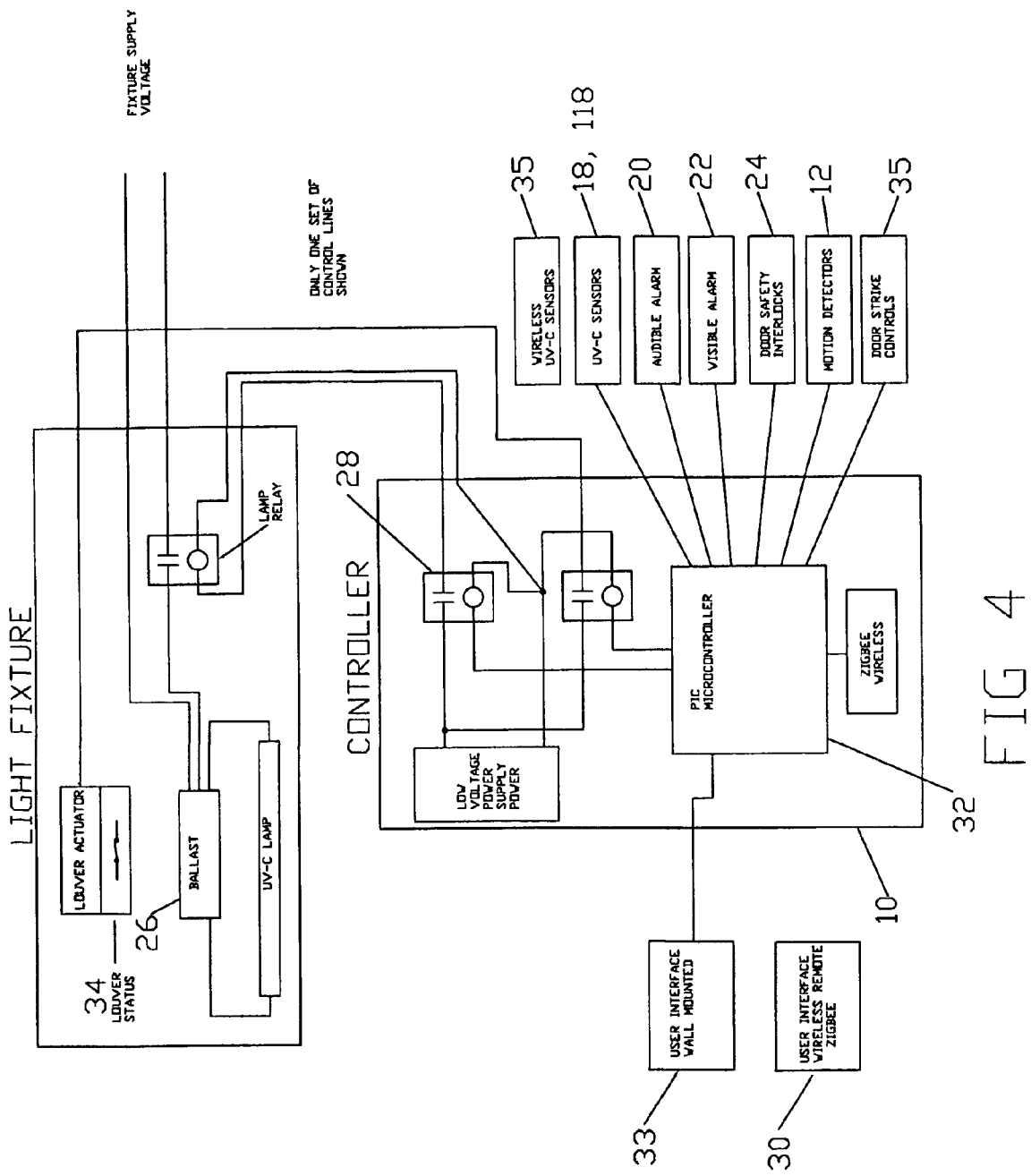

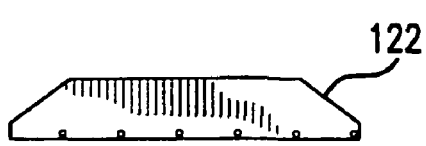
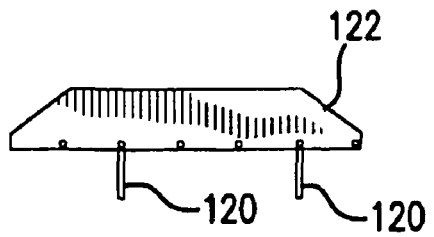
FIG.5A  FIG.5B
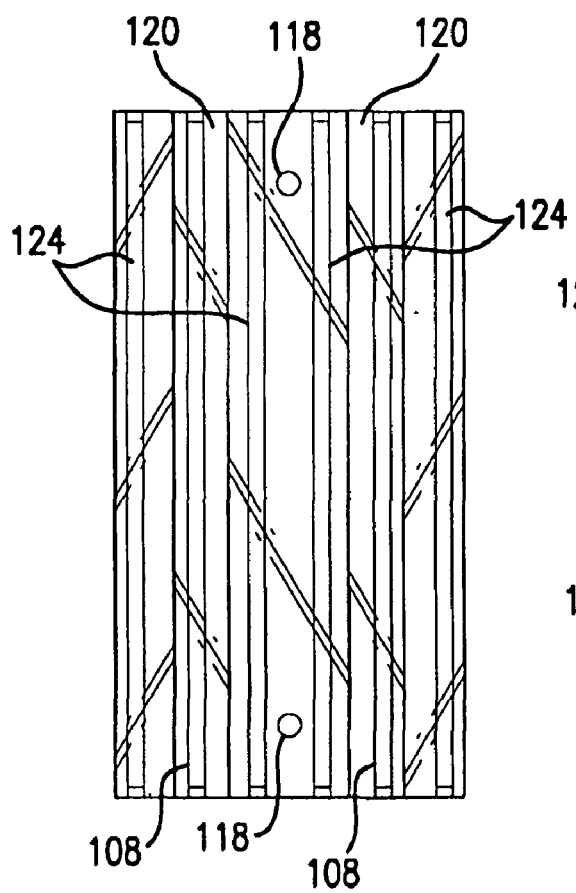
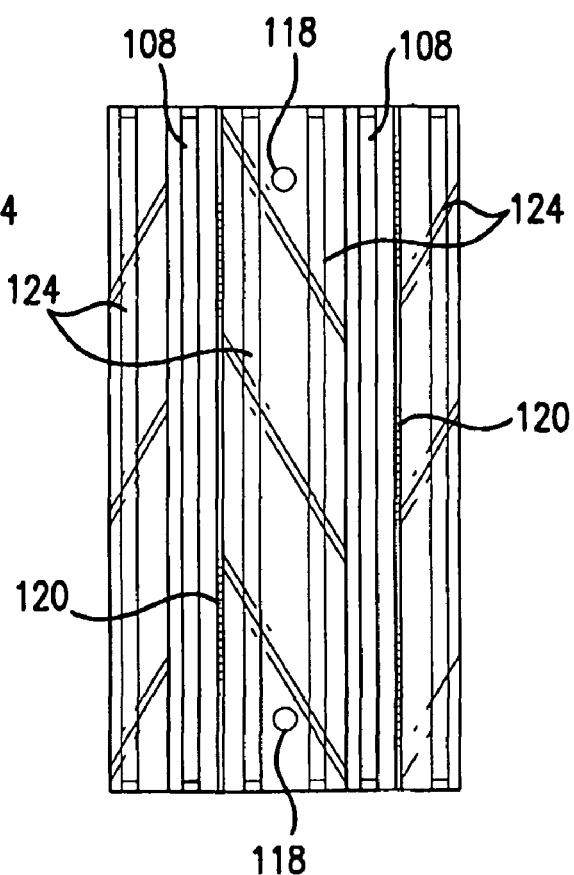
FIG.6A  FIG.6B

AREA STERILIZER AND METHOD OF DISINFECTION

This application claims priority of provisional application Ser. No. 61/024,373, filed Jan. 29, 2008; and provisional application Ser. No. 61/083,590, filed Jul. 25, 2008.

FIELD OF THE INVENTION

This invention relates to methods and devices for bacterial, fungal and/or viral sterilization and disinfection, and is more particularly directed to a method and device for disinfecting rooms and similar enclosed areas.

BACKGROUND OF THE INVENTION

Nosocomial, or hospital acquired, infections are common, costly, and sometimes lethal. A recent review of such infections in the cardiac surgery unit of a major hospital revealed a nosocomial infection rate of 27.3% that more than doubled the mortality rate for afflicted patients. The nature of bacteria acquired in the hospital setting differs significantly from bacteria found in a community setting primarily in their resistance to antibiotic therapy.

"Historically, staphylococci, pseudomonads, and *Escherichia coli* have been the nosocomial infection troika; nosocomial pneumonia, surgical wound infections, and vascular access-related bacteremia have caused the most illness and death in hospitalized patients; and intensive care units have been the epicenters of antibiotic resistance. Acquired antimicrobial resistance is the major problem, and vancomycin-resistant *Staphylococcus aureus* is the pathogen of greatest concern. The shift to outpatient care is leaving the most vulnerable patients in hospitals. Aging of our population and increasingly aggressive medical and surgical interventions, including implanted foreign bodies, organ transplantations, and xenotransplantation, create a cohort of particularly susceptible persons. Renovation of aging hospitals increases risk of airborne fungal and other infections.

Significant morbidity, mortality, and costs are associated with these infections. Many factors contribute to these dangerous infections. Most notably is the overuse of antibiotics and poor personal hygiene such as hand washing. Abundant evidence exists, however, that the hospital environment itself contributes to the problem by harboring virulent strains of bacteria, fungi, and viruses, and that many methods commonly used are ineffective and may actually spread contaminants.

Attempts to eradicate surface contaminates from the hospital setting have varied greatly in strategy and success. These have ranged from antiseptic soaps to fumigation with formaldehyde gas. Topical antiseptics are problematic for several reasons. First, they have recently been shown to actually induce antibiotic resistances and thus may be adding to the problem. Secondly, many surfaces such as keyboards, television sets, and monitoring controls are difficult if not impossible to decontaminate with liquid disinfectants without harming the electronics. Gas disinfection, while effective, is time consuming, hazardous to workers, and environmentally unwise.

Ultraviolet (UV) light has been long used for disinfection and sterilization. Ultraviolet light may be produced artificially by electric-arc lamps. Recently, the widespread availability of low to medium pressure mercury bulbs has led to the development of devices which use UV-C to decontaminate water supplies. UV-C is a high frequency wavelength of light within the ultraviolet band and has been shown to be the most bactericidal type of ultraviolet light. UV-C has wavelengths of about 2800 Å to 150 Å. To date, there are no published efforts to use UV-C to decontaminate or disinfect larger areas such as operating rooms. The only recent availability of the appropriate bulbs as well as significant safety concerns regarding worker exposure to UV-C likely contribute to the lack of efforts to use UV-C outside of self-contained water purification systems.

SUMMARY OF THE INVENTION

An ultraviolet area sterilizer or disinfector is incorporated into a building structure where concern exists regarding the presence of pathogens on environmental surfaces. Ultraviolet C (UV-C) generators generate UV-C that is directed to architectural partitions of an enclosed area. The architectural partitions reflect UV-C to kill pathogens in the enclosed area. The device transmits a calculated dose of UV-C from a fixture mounted to an architectural partition in the enclosed area. Once an effective cumulative dose of UV-C has been reflected to radiation sensors, as measured by the sensors, the device shuts down.

DESCRIPTION OF THE DRAWINGS

FIG. 4 is a schematic of the controls of the device.
FIG. 5A is an elevation of a lighting fixture that incorporates UV-C bulbs.
FIG. 5B shows the fixture of FIG. 5A with louvers in an open position for actuation of the bulbs.
FIG. 6A is a bottom plan view of a lighting fixture that incorporates UV-C bulbs
FIG. 6B shows the fixture of FIG. 6A with louvers in an open position for actuation of the bulbs

DETAILED DESCRIPTION OF THE PREFERRED EMBODIMENT

Figure 1:
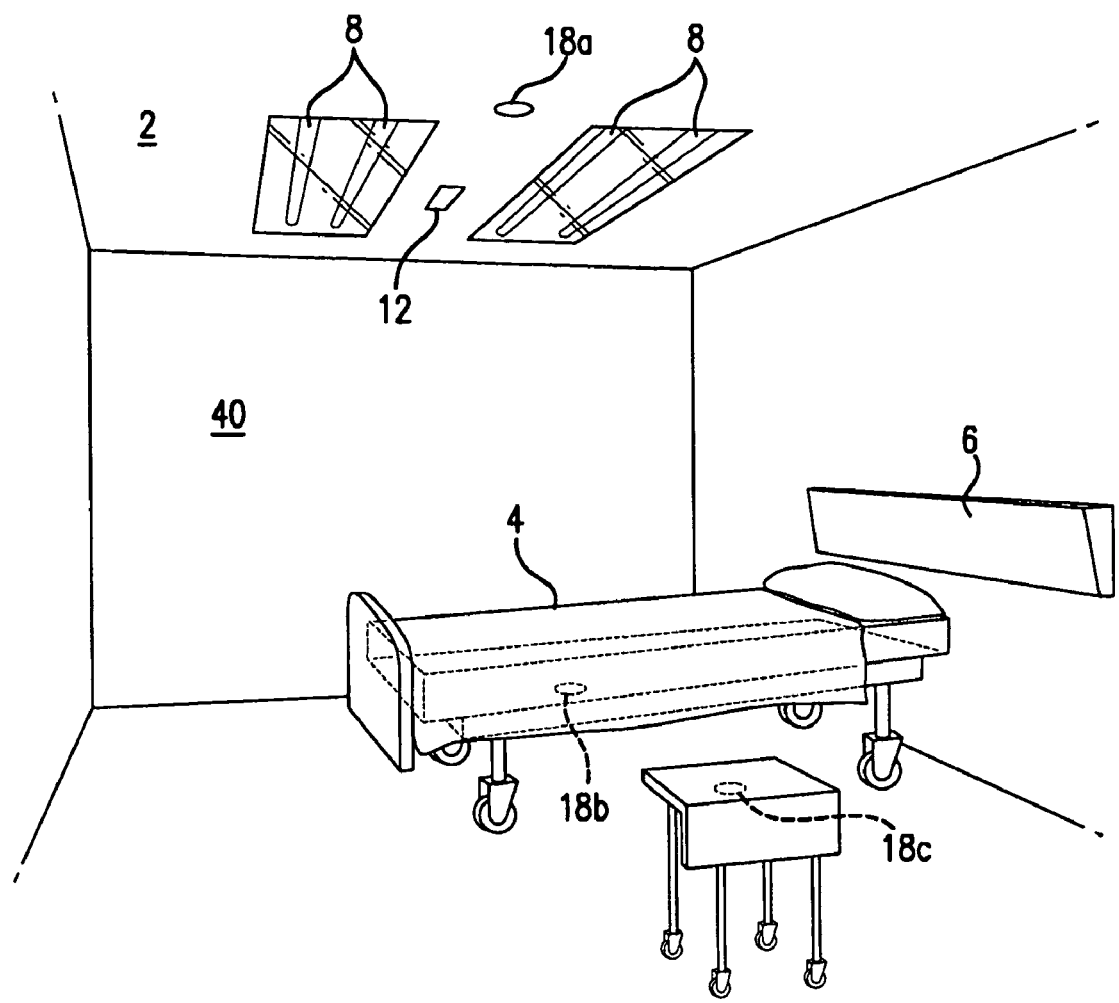
FIG. 1 is a perspective view of a medical facility room incorporating the invention.

Referring now to the drawing figures, banks of UV-C emitting bulbs 8 are positioned in an architectural partition, which could be a wall, but may be a ceiling 2 of the enclosed area. The enclosed area may be a room located in a building. FIG. 1.

Figure 2:
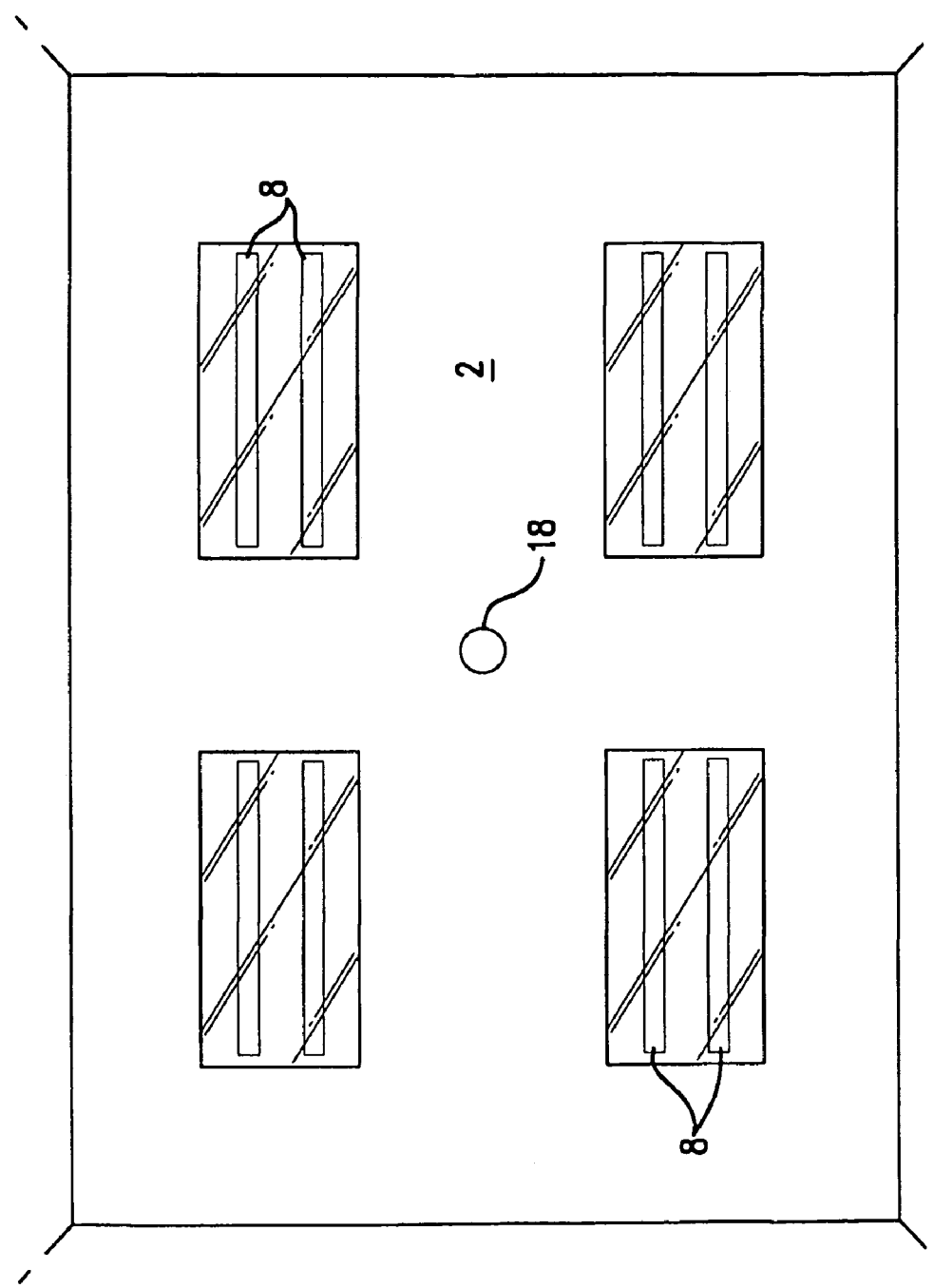
FIG. 2 is a plan view of an array of bulbs.
Figure 3:
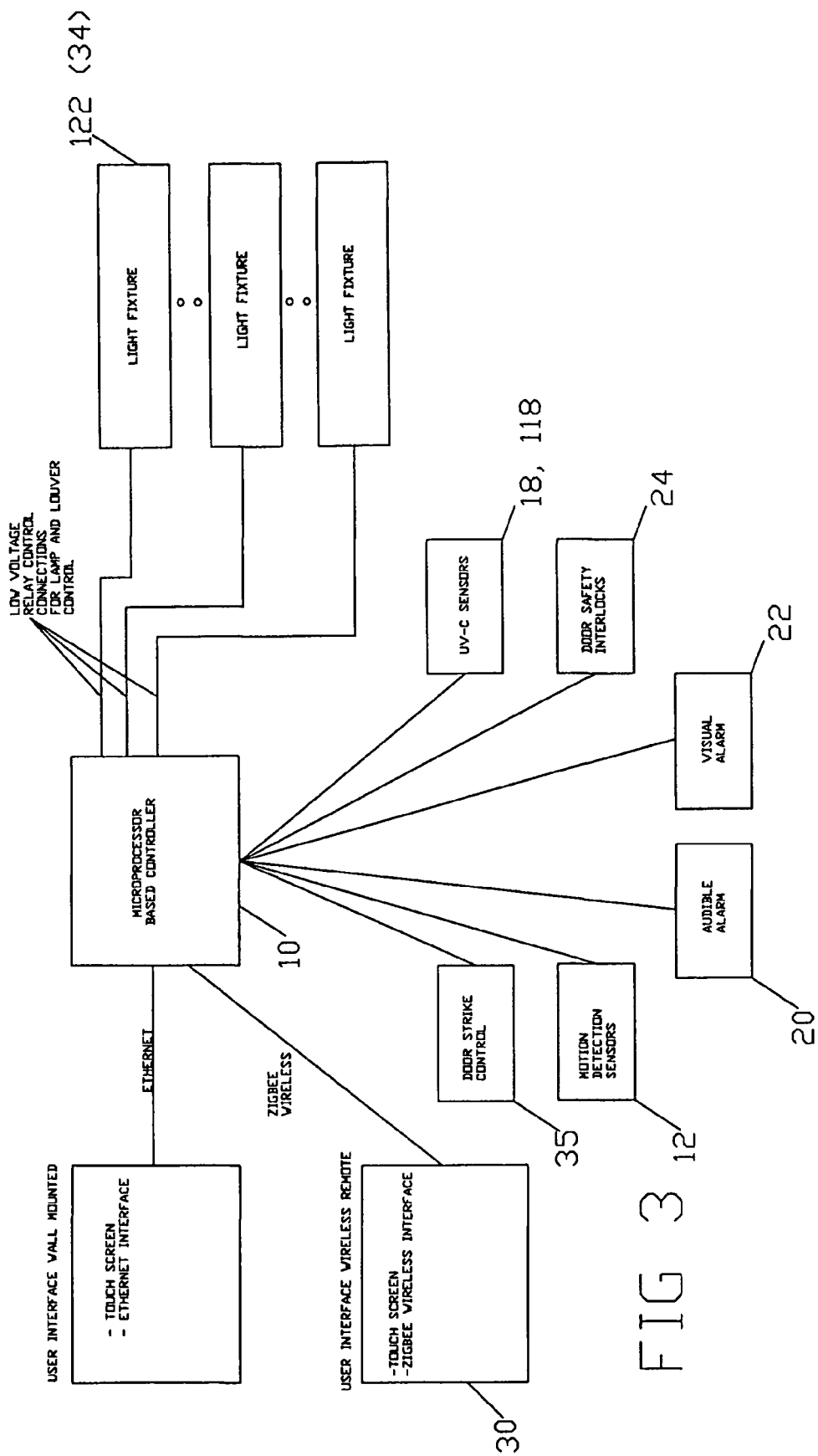
FIG. 3 is a schematic of the device.

In one embodiment, four (4) pairs of medium pressure mercury bulbs may be present in a fixture that is located in a ceiling of a room. FIG. 2. The bulbs may be 48-inch long, 115-Watt UV-C generating lamps or bulbs that produce 300 microwatts of ultraviolet radiation at 1 meter. Other effective UV-C generators or bulbs may be used. Each pair of bulbs is positioned to provide coverage of the entire room. The lamps or bulbs may be positioned between ceiling tiles that are commonly used in commercial buildings, including hospitals and medical clinics. The lamps or bulbs may be positioned in a similar manner to fluorescent bulb arrays that are used as lighting in buildings.

One advantage of using the bulbs in multiple fixtures, with the fixtures affixed to walls and/or ceilings of real property is that broad coverage of the room may be achieved, with the UV-C radiation emanating from multiple locations that are remote from each other and over a relatively large area. Optimal positioning of the bulbs according the requirements of the particular room may be achieved. If a portable unit is used, the dissemination of UV-C radiation is limited to a radius around the machine.

A base, such as a lighting fixture, is provided for the lamps or bulbs. The base or fixture may be positioned in the ceiling between ceiling tiles and/or HVAC outlets. The lamps or bulbs are positioned to direct UV-C radiation from overhead toward the room structure, and toward furniture 4, fixtures 6 and equipment within the room. The UV-C radiation is reflected from surfaces in the room, and particularly, the flat and preferably light colored wall surfaces, so that the UV-C radiation is received both directly and indirectly, by reflection, to surfaces in the room. Surfaces that are not in a direct, unobstructed line with the UV-C emitters will receive UV-C radiation in a dosage that is effective to achieve adequate disinfection of the room due to reflection from other surfaces in the room.

UV-C sensors, such as sensor 18a, may be mounted in the ceiling, such as in ceiling tiles, and positioned so as to receive reflected radiation that is reflected from objects in the room or the walls and floors of the room, without receiving material levels of UV-C radiation directly from the UV-C lamps. That is, one or more of the sensors may be mounted in the same flat, planar architectural partition as the UV-C bulbs or emitters so that the sensors do not receive direct radiation, but rather, they receive reflected radiation that is reflected from surfaces in the room. The bulbs 8 are preferred to be recessed within a fixture, and the sensor may also recessed within a ceiling or similar plane, so that the sensor does not receive direct radiation from the bulbs.

Sensors may be mounted on fixtures or objects located in the room. Multiple sensors may be positioned in the room. None of the sensors shown in FIG. 1 receive a material dose of UV-C radiation directly from the UV-C bulbs. Sensors 18b and 18c are shown as being positioned under objects in the room, such as beds, tables or other furniture 4, equipment or fixtures. These sensors are positioned so that they do not receive direct radiation from the UV-C bulbs 8. Similarly, sensor 18a, by being positioned in the ceiling, does not receive direct radiation from the UV-C bulbs, but only such UV-C radiation as is reflected to it.

In another embodiment, the bulbs 18 are mounted below the ceiling, but just below the ceiling. The bulbs should be at least two (2) meters above the floor, and it is preferred that the highest bulb is mounted not more than 15 centimeters from the ceiling. In one embodiment, the bulbs are mounted in one or more corners of the enclosed area or room, and are positioned for maximum reflectivity toward the darkest corner of the room. In an embodiment, the bulbs are mounted in a room in a corner and just below the ceiling, with the bulbs directed to a diagonally opposite corner of the room that is the darkest corner of the room. The darkest corner of the room is the corner that is measured to receive the lowest level of reflected radiation. If the run time of the bulbs, as determined by the cumulative dosage received by the sensors, exceeds a pre-set time limit, then an additional bulb or bulbs, spaced apart from other arrays of bulbs, should be added.

In one embodiment, a sensor is mounted in the same corner of a room or enclosed area as an array of bulbs. The sensor is positioned so as to not receive direct radiation. The sensor is positioned within and surrounded by a surround which acts to shield to shield the receiver sensor from direct radiation, but allows reflected radiation to be received. This may be accomplished in one embodiment by placing the sensor in a tube, with an opening in the end of the tube allowing the sensor to receive reflected radiation.

FIGS. 5A, 5B, 6A, and 6B show an embodiment of UV-C emitting bulbs 108 positioned in a light fixture. The light fixture 122 may be mounted in a ceiling, such as a light fixture that is positioned between ceiling tiles. In this embodiment, fluorescent light bulbs 124 of a type that are generally in use are also present in the fixture. Bulbs 124 provide visible light for lighting the room and may be operated by a wall switch.

UV-C sensors 118 are present in the fixture 122. The sensors are preferred to be spaced apart from the UV-C emitting bulbs and mounted in the fixture so that they receive UV-C radiation that is reflected from surfaces in the room, and particularly surfaces that are below the bulbs 108, and the sensors do not receive material levels of direct UV-C radiation from the bulbs.

The embodiment of the light fixture shown in FIG. 5 and FIG. 6 uses louvers 120 as a safety device to prevent inadvertent discharge of UV-C radiation when people are in the room, motion is detected, or if objects are in the room that should not be present. The louvers also protect the UV-C bulbs, and help discourage service or replacement by unauthorized persons.

The covers or louvers 120 may be formed of an opaque material that prevents visible light and UV-C radiation from passing through. Alternatively, the covers or louvers may be formed of a material that is substantially transparent or translucent to visible light, but prevents or filters UV-C radiation from passing through the cover.

In one embodiment, the covers or louvers are movable and are movable in response to commands from the control system. Upon actuation of the device, the louvers are moved by actuators from the position (closed) shown in FIGS. 5A and 6A to the position (open) shown if FIGS. 5B and 6B to reveal the bulbs and permit treatment of the room. Upon completion, the actuators move the louvers to the closed position. The actuators may be driven by electric motors which rotate a drive train to rotate the louvers from the closed position into the open position and back to the closed position. Solenoids may also be used to move the louvers. A feedback device may be employed to provide open or closed louver status. A louver interlock mechanism may be included to prevent accidental activation of the lamps.

If coverage of the room cannot be accomplished by arrays of lamps positioned in the walls, the lamps or bulbs may be supplemented with lamps or bulbs positioned within the ceiling. It is preferred that the UV-C emitters are positioned overhead, so that the lamps are not easily reached by persons in the room. Further, positioning the lamps overhead gives the best chance of unobstructed emission of the UV-C radiation and reflection of the radiation, and particularly reflection from wall surfaces. The lamps or bulbs are spaced apart as necessary to achieve UV-C coverage that effectively kills pathogens in the room and within a reasonable time, such as less than about twenty (20) minutes for an operating suite. Portable lamps or bulbs may also be used, with the portable lamps positioned as required within the room. The position of the portable lamps may be dictated by the position of furniture or equipment that is located, or relocated, within the room.

In one embodiment, a control box 10 contains components such as a PIC Microcontroller 32 and redundant control relays 28. Motion detectors 12, door interlocks 24 or door strike controls 35, louver status 34, and audible 20 and visible alarms 22 are preferred to be employed for safety. An embodiment of one control structure using a PIC Microcontroller is hereinafter described.

Referring now to FIG. 4, door interlocks 24 are shown. These interlocks are activated by the doors of the room in which the device is operating. The door interlocks are switches which disable the device if any one of the switches is opened, such as by opening the door. Door strike controls 35 would not allow the door to be opened while the device is activated. The motion detectors 12 are immediately monitor upon activation of the device and prior to powering of the ballasts 26 and the bulbs, by means of a relay 28. If the motion detectors sense motion at any time during the operation of the device, power to the ballasts and the bulbs is immediately disabled.

The device may be controlled by a programmable PIC Microcontroller 32 (PIC). The PIC is contained in the control box 10. PIC® Microcontrollers, available from Microchip Technology, Inc of Chandler, Ariz. may be used.

The PIC Microcontroller continuously receives a voltage input from sensors, such as sensors 18, 118, which receive reflected UV-C radiation, although sensors receiving direct radiation may also be monitored. Upon initiation of the device, the sensors continuously sense and measure the level of UV-C radiation which is reflected back to the device. It is preferred that the cumulative UV-C radiation emission is measured from initiation of the emission to termination for each of the sensors. Ideally, reflections from substantially all points in the room will be measured. Placement of the sensor and the number of sensors to be used will be determined by the size, architecture and contents of the room. For example, eight or more sensors that are strategically positioned may be used. Wireless remote UV-C sensors 35 may also be employed to monitor a specific area of concern.

If the device is ceiling mounted according to a preferred embodiment of the device, at least one sensor will typically be positioned in the ceiling to receive reflected radiation from the bulbs that are directed away from the ceiling. A sensor or sensors may be positioned in the lighting fixture, but is preferred that the sensor or sensor be positioned so as to receive reflected radiation without receiving UV-C radiation directly from the UV-C bulbs.

Each sensor converts the measurement of the level of radiation to a voltage output, which is transmitted to the PIC. The PIC samples the voltage received at intervals and adds the cumulative total of the voltage received. When the PIC determines that the reflected UV-C radiation received by each and every sensor has reached the predetermined minimum cumulative total, the PIC causes the device to shut down, and a signal is given to the operator that the process has been completed. The PIC is programmable to measure voltage inputs as required by the particular application.

The PIC receives commands from a control, which may be a wireless remote control 30, or it maybe hardwired to the other operating components 33. The control may be mounted on a wall, but should be mounted outside of the enclosed area or room to be treated so that the control can be operated without exposing the operator to UV-C radiation.

A switch activates the remote control. Entry of a security code allows the operator to begin sending commands to the PIC. Commands include Activate, Shutdown, enter Sterilization Mode, or enter Sanitize Mode. The remote is in two-way communication with the device and displays data from the sensor array, time left to sterilize or sanitize the room, and in case of bulb failure, the status of all numbered bank of bulbs. If two-way communication with the remote is lost, the device shuts down.

The PIC monitors the motion detectors at least one minute prior to activation of the UV-C bulbs and continues to monitor the detectors during the cycle. The PIC performs all calculations regarding bactericidal doses, stores cumulative dosing data, and system checks to alert the operator of bulb failure. This is needed since an operator should not look at the bulbs to check for burned out bulbs or damaged banks. The PIC can be reprogrammed by attaching a personal computer via a data bus connection, thus allowing alteration to the algorithms to accommodate special circumstances.

An example of a protocol for using an embodiment of the device is described. An operator checks the room for occupants, then leaves the room. After securing the room, the operator enters into the control a security code or password, whereupon the operator is prompted to press an "on" switch on the control, activating the device. The audible voice alarms and the motion detectors activate and are preferred to stay on until the entire cycle has been complete. Should the device detect motion, the device automatically deactivates itself until the operator re-enters the room to clear the room, thus preventing the operator from re-activating the device and harming an occupant present in the room.

One or more motion detectors are monitored for a preset time, such as one minute, prior to opening the louvers and powering the UV-C bulbs, and then stay active until the cycle is complete, the bulbs are powered down and the louvers closed. The array of bulbs according to the embodiment shown in the drawings emits UV-C radiation downwardly to at a preferred minimum angle of 150 degrees, and more preferably, at substantially 180 degrees, from the array of bulbs, so that all working and occupied surfaces that are below the array of bulbs and are within the enclosed area are exposed to UV-C radiation. As seen in FIG. 1, all furniture, fixtures and objects that are in a direct line with the bulbs 8 will receive direct radiation.

Sensors are positioned so as to not receive direct output from the germicidal lamps, thus measuring the dose of UV-C reflected back to the sensors. This data is fed into the microcontroller where it is integrated to compute cumulative exposure of UV-C reflected back from each sensor in the array.

In one embodiment, reflecting from the least reflective surface or direction the microcontroller calculates the time the device stays activated to allow an effective dose of UV-C to be emitted within the enclosed area. Several thousand measurements or "snapshots" may be taken for computation of the cumulative dosage.

Once sufficient time for a lethal dose of UV-C to be reflected back to the sensors has elapsed, and the minimum cumulative dosage corresponding to each sensor is received by the corresponding sensor, the device may power down the bulbs and sound an "all clear" alert to the operator. If the device uses louvers or similar movable covers for the fixture, then the louvers may move to a closed position that covers the UV-C emitters or bulbs.

Upon completion of the cycle, the device is preferred to have disinfected all the exposed surfaces within the room, including the primary shadows such as the back or wall side of all rails, cabinets which are not against the wall, and tables. Surfaces not directly exposed to the UV-C radiation may be sterilized by UV-C radiation reflected from the walls and ceilings.

In most environments, there is a presence of what microbiology labs label as "wild spore forms" of bacteria. These bacteria are not known to cause human disease, and yet, are resistant to low doses of UV-C. The dual programming modes of one embodiment of the device allow treatment as required. One mode (Sanitize) kills all known pathogens and requires a lower exposure and thus shorter time. The other mode (Sterilize) kills all species of bacteria and requires greater cumulative doses and therefore more time.

Without adequate safety features, daily use of intense UV-C is dangerous and impractical. The device may have motion detectors which assure the room is vacant of personnel prior to activation. Once activated, the device shuts down instantly when motion occurs anywhere in the room being disinfected. If the device loses two-way communication with the control panel it also shuts down. In daily use, safety protocols commonly used in hospitals such as those in use for laser and x-ray devices may be implemented.

The device is able to sanitize or sterilize all exposed surfaces in a room. It is able to do so safely, leave no residual toxins or radiation, and generates no adverse environmental side products. In addition, the device is able to notify the operator of the time required to perform this task and automatically shuts down upon completion of sterilization. The inventor has performed tests to prove the efficacy of the device, all of which have been successful. Reflectivity of some paints and other surfaces which absorb rather than reflect UV-C, requiring prolonged exposures of twenty minutes or greater. Specially reflective paints are preferred to be included in the system of area sterilization presented by this invention.

The estimated reflection from the wall in a typical hospital room was only 3%. Reflection below three percent is not desirable, since the increased exposure time required to achieve an effective dose may result in degradation of articles which are present in the room and which are exposed to direct UV-C radiation. A minimum of five (5%) percent reflectivity is desired. Through the use of paint or coating that produces a painted wall reflecting 50-85% of the UV-C, the efficiency of the device is increased, allowing for greatly decreased exposure times.

It is preferred to have the walls of the room, and other painted surfaces in the room, covered with paint or a similar coating. The paint or coating should have UV-C reflectivity enhancing materials, which may be pigments, in the paint 40. The reflective particles or pigments may be colorants. In one embodiment, the coating includes particles of barium sulfate that will reflect the UV-C radiation. This coating may be transparent to the naked eye, and used to cover painted surfaces such as painted walls or cabinets. In another embodiment, aluminum oxide is used as a pigment that will enhance reflectivity of the UV-C radiation. It is preferred that the paint or coating not have titanium dioxide in a form that absorbs ultraviolet radiation. The paint or coating should be free of materials that are added to the paint or coating for the purpose of absorbing ultraviolet radiation.

What is claimed is:

1. A device for disinfecting an enclosed area by use of ultraviolet radiation, comprising:
    a fixture that is attached to a fixed architectural partition that forms a part of the enclosed area and is positioned overhead in the enclosed area;
    an ultraviolet-C radiation emitter located in said fixture, wherein the ultraviolet-C radiation emitter is positioned to direct ultraviolet-C radiation from overhead and toward a wall of the enclosed area; and
    a plurality of radiation sensors that are positioned with the enclosed area and spaced apart from each other and apart from the fixture, and the plurality of radiation sensors are positioned in the enclosed area and below the ultraviolet-C radiation emitter to receive ultraviolet-C radiation emitted by the ultraviolet-C radiation emitter and reflected from the wall of said enclosed area, wherein said ultraviolet-C radiation reflected from the wall to said plurality of sensors is measured, and a controller terminates emission of ultraviolet-C radiation from said ultraviolet-C radiation emitter after a predetermined accumulated dosage of radiation is received by each of said radiation sensors.

2. A device for disinfecting an enclose area by use of ultraviolet radiation as described in claim 1, wherein said fixed architectural partition is a ceiling, and said fixture and said ultraviolet-C radiation emitter located in said fixture are attached to said ceiling.

3. A device for disinfecting an enclosed area by use of ultraviolet radiation as described in claim 1, wherein said fixed architectural partition is a ceiling, and said fixture and said ultraviolet-C radiation emitter located in said fixture are attached to said ceiling, and wherein a radiation sensor that receives ultraviolet-C radiation reflected from architectural partitions is attached to said ceiling and positioned so as to not receive direct ultraviolet-C radiation from said ultraviolet-C emitter attached to said ceiling.

4. A device for disinfecting an enclosed area by use of ultraviolet radiation, as described in claim 1, wherein said fixture that is attached to the fixed architectural partition of the enclosed area comprises a cover that blocks ultraviolet-C radiation emission, and wherein said cover is positioned over said ultraviolet-C radiation emitter located in said fixture to cover said ultraviolet-C radiation emitter when said ultraviolet-C radiation emitter is not in operation, and wherein said cover is moved away from covering said ultraviolet-C radiation emitter when said ultraviolet-C radiation emitter is in operation to allow ultraviolet-C radiation to be emitted into said enclosed area, and wherein said cover covers said ultraviolet-C radiation emitter when said controller causes termination of emission of ultraviolet-C radiation from said ultraviolet-C radiation emitter.

5. A device for disinfecting an enclosed area by use of ultraviolet radiation as described in claim 1, wherein a first radiation sensor that receives ultraviolet-C radiation reflected from architectural partitions is located on one of said architectural partitions and a second radiation sensor is located underneath equipment or furniture that is present is said enclosed area, and the second radiation sensor is positioned below the ultraviolet-C radiation emitter, wherein first radiation sensor and said second radiation sensor each receive reflected ultraviolet-C radiation and measure said reflected ultraviolet-C radiation and cause termination of emission of ultraviolet-C radiation from said ultraviolet-C radiation emitter after a predetermined accumulated dosage of radiation is received by each of said first radiation sensor and said second radiation sensor.

6. A device for disinfecting an enclosed area by use of ultraviolet radiation as described in claim 1, wherein said fixed architectural partition is a second wall of the enclosed area, and said fixture and said ultraviolet-C radiation emitter located in said fixture are attached overhead and to said second wall.

7. A device for disinfecting an enclosed area by use of ultraviolet radiation as described in claim 1, wherein said fixture further comprises a light emitter that emits visible light.

8. A device for disinfecting an enclosed area by use of ultraviolet radiation, as described in claim 1, wherein said fixture further comprises a light emitter that emits visible light, and said fixture further comprises a cover that blocks ultraviolet-C radiation emission while said cover simultaneously permits emission of visible light.

9. A device for disinfecting an enclosed area by use of ultraviolet radiation, as described in claim 1, wherein said wall of said enclosed area is coated so as to reflect not less than five (5%) percent of the ultraviolet-C radiation directed at said wall.

10. A device for disinfecting an enclosed area by use of ultraviolet radiation as described in claim 1, wherein said fixed architectural partition is a ceiling, and said fixture and said ultraviolet-C radiation emitter located in said fixture are attached to said ceiling, and wherein a second fixed architectural partition is a second wall, and a second fixture and a second ultraviolet-C radiation emitter located in said second fixture are attached to said second wall, and wherein said fixture and said second fixture are spaced apart.

11. A device for disinfecting an enclosed area by use of ultraviolet radiation, as described in claim 1, wherein said fixture that is attached to the fixed architectural partition of the enclosed area comprises a cover that blocks ultraviolet-C radiation emission, and wherein said cover is positioned over said ultraviolet-C radiation emitter located in said fixture to cover said ultraviolet-C radiation emitter when said ultraviolet-C radiation emitter is not in operation, and wherein said cover is moved away from covering said ultraviolet-C radiation emitter when said ultraviolet-C radiation emitter is in operation to allow ultraviolet-C radiation to be emitted into said enclosed area, and wherein said cover covers said ultraviolet-C radiation emitter when said controller causes termination of emission of ultraviolet-C radiation from said ultraviolet-C radiation emitter or when a motion sensor located in said enclosed area senses motion.

12. A device for disinfecting an enclosed area by use of ultraviolet radiation, as described in claim 1, wherein the ultraviolet-C radiation emitter is positioned overhead and in a corner of the enclosed area and the ultraviolet-C radiation emitter is positioned to direct ultraviolet-C radiation to the wall.

13. A device for disinfecting an enclosed area by use of ultraviolet radiation, as described in claim 1, wherein the ultraviolet-C radiation emitter is positioned overhead in a corner of the enclosed area to direct ultraviolet-C radiation from overhead to a diagonally opposite corner of the enclosed area that comprises the wall.

14. A device for disinfecting an enclosed area by use of ultraviolet radiation, as described in claim 1, wherein the ultraviolet-C radiation emitter is positioned adjacent to a ceiling of the enclosed area and generally horizontally to direct ultraviolet-C radiation from overhead and downwardly toward the wall of the enclosed area, and wherein the ultraviolet-C radiation emitter is positioned to direct ultraviolet-C radiation at the wall and toward the enclosed area at an angle of not less than 150 degrees from the plane of the ceiling.

15. A device for disinfecting an enclosed area by use of ultraviolet radiation, as described in claim 1, further comprising a second fixture that is attached to a fixed architectural partition that forms a part of the enclosed area and is positioned overhead in the enclosed area; and an ultraviolet-C radiation emitter located in the second fixture, wherein the ultraviolet-C radiation emitter is positioned to direct ultraviolet-C radiation from overhead and toward a second wall of the enclosed area.

16. A device for disinfecting an enclosed area by use of ultraviolet radiation, as described in claim 1, wherein the ultraviolet-C radiation emitter located in the fixture is positioned to direct ultraviolet-C radiation to the entirety of the enclosed area from overhead.

17. A device for disinfecting an enclosed area by use of ultraviolet radiation, as described in claim 1, wherein a sensor of the plurality of sensors is recessed in the fixed architectural partition in the enclosed area.

18. A device for disinfecting an enclosed area by use of ultraviolet radiation, as described in claim 1, wherein a sensor of the plurality of sensors is positioned within a device comprising a shield and said device is positioned to shield the sensor from receiving direct radiation from the ultraviolet-C radiation emitter.

* * * * *